(12) United States Patent
Ramzan et al.

(10) Patent No.: US 10,281,423 B1
(45) Date of Patent: May 7, 2019

(54) FUEL QUALITY SENSOR

(71) Applicant: UNITED ARAB EMIRATES UNIVERSITY, Al Ain (AE)

(72) Inventors: Rashad Ramzan, Al Ain (AE); Omar Farooq Siddiqui, Al Ain (AE); Nabil Bastaki, Al Ain (AE)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 15/812,693

(22) Filed: Nov. 14, 2017

(51) Int. Cl.
*G01N 27/22* (2006.01)
*G01N 27/24* (2006.01)
(Continued)

(52) U.S. Cl.
CPC ........... *G01N 27/221* (2013.01); *G01N 27/24* (2013.01); *G02B 6/4298* (2013.01); *G01N 22/04* (2013.01); *G01N 27/02* (2013.01)

(58) Field of Classification Search
CPC ........ G01N 27/00; G01N 27/02; G01N 27/22; G01N 27/221; G01N 27/24; G01N 22/00; G01N 22/04; G01N 21/7746; G01N 2021/7789; G02B 6/00; G02B 6/24; G02B 6/42; G02B 6/4298; G01R 19/00; G01R 19/2506; G01R 23/00; G01R 23/16; G01R 27/00; G01R 27/26; G01R 27/2605; G01R 27/28; G01D 5/00; G01D 5/12; G01D 5/14; G01D 5/24; G01D 5/2405; G06F 3/044
USPC ....... 324/600, 629, 633, 634, 636, 637, 639, 324/640, 642, 643, 649, 658, 663, 664, 324/76.11, 76.12, 76.19, 76.21, 76.22, 95
See application file for complete search history.

(56) References Cited

U.S. PATENT DOCUMENTS 5,164,675 A 11/1992 Howe et al.
5,435,170 A 7/1995 Voelker et al.
(Continued)

FOREIGN PATENT DOCUMENTS

JP 3-249553 A 11/1991
WO WO 2014/009468 A1 1/2014

OTHER PUBLICATIONS

Siddiqui et al., "Dielectric Sensors Based on Electromagnetic Energy Tunneling," Sensors, 15(4), 7844-7856, Mar. 31, 2015.
(Continued)

*Primary Examiner* — Hoai-An D. Nguyen
(74) *Attorney, Agent, or Firm* — Richard C. Litman

(57) ABSTRACT

The fuel quality sensor includes two rectangular parallepiped waveguides of equal dimensions stacked one atop the other and having a common ground. A thin wire extends through the intermediate wall(s) between the upper and lower waveguide cavities. An input connector is mounted on a sidewall of the upper waveguide, and an output connector is mounted on a sidewall of the lower waveguide cavity. A fluid conduit extends through the upper waveguide cavity adjacent the wire. A tunable microwave signal or wideband time domain pulse is applied to the input connector while fuel is flowing through the conduit. If the fuel flowing in the conduit is uncontaminated, the output signal at the second connector will show no change from the tunneling frequency, but if the fuel is contaminated, the change in the fuel's dielectric constant will result in a change in tunneling frequency and/or tan δ at the second connector.

11 Claims, 7 Drawing Sheets

(51) Int. Cl.
*G02B 6/42* (2006.01)
*G01N 22/04* (2006.01)
*G01N 27/02* (2006.01)

(56) References Cited

U.S. PATENT DOCUMENTS

| | | | |
|---|---|---|---|
| 5,604,441 A | 2/1997 | Freese et al. | |
| 6,247,246 B1 * | 6/2001 | Scalese | G01N 5/045 |
| | | | 219/678 |
| 6,494,079 B1 * | 12/2002 | Matsiev | G01H 13/00 |
| | | | 73/24.05 |
| 6,707,307 B1 * | 3/2004 | McFarlane | G01N 22/00 |
| | | | 324/617 |
| 6,755,086 B2 * | 6/2004 | Salamitou | G01F 1/44 |
| | | | 73/861.04 |
| 6,915,707 B2 * | 7/2005 | Nyfors | G01F 1/40 |
| | | | 73/861.63 |
| 8,746,045 B2 * | 6/2014 | Carvalho | G01F 23/284 |
| | | | 702/50 |
| 9,510,708 B2 * | 12/2016 | Behle | A47J 37/1223 |
| 9,816,914 B2 * | 11/2017 | Baigar | G01N 21/05 |
| 9,835,573 B2 * | 12/2017 | Herb | G01N 27/02 |
| 2003/0222656 A1 | 12/2003 | Phillips et al. | |
| 2009/0129527 A1 * | 5/2009 | Joo | G21C 19/205 |
| | | | 376/249 |
| 2014/0331785 A1 * | 11/2014 | Ao | G10K 11/00 |
| | | | 73/861.18 |
| 2015/0192558 A1 | 7/2015 | De Coninck et al. | |

OTHER PUBLICATIONS

Silveirinha et al., "Tunneling of Electromagnetic Energy through Subwavelength Channels and Bends using e-Near-Zero Materials", Physical Review Letters (2006), 4 pages, 97:15.

Liu et al., "Experimental Demonstration of Electromagnetic Tunneling Through an Epsilon-Near-Zero Metamaterial at Microwave Frequencies", Physical Review Letters (2008), 4 pp.

* cited by examiner

FUEL QUALITY SENSOR

BACKGROUND

1. Field

The disclosure of the present patent application relates to fuel for internal combustion engines, and in particular to an electronic real-time fuel quality sensor for detecting contaminants in fuel flowing in a conduit using electromagnetic energy tunneling.

2. Description of the Related Art

The real-time monitoring of fuel quality during long term storage and transportation is highly desirable. If the quality of fuel is not properly examined, then any contaminated fuel may cause one or more of the following: corrosive deposition on engine parts; reduced heat of combustion; engine component wear (such as turbine blade wear); filter clogging; microbial-influenced corrosion; sludge formation; etc. Growth of microbes, such as bacteria and fungi, due to vent air, dust, and corruption from water content in fuel due to leakage in floating tank and underground tanks are primary causes of fuel contamination. The contamination may affect such fuel properties as color, density, viscosity, thermal stability and dielectric permittivity (Dk). The effect of different types of contamination on fuel properties are shown in Table 1.

TABLE 1

Effect of Contaminants on Fuel Quality

| Contamination | Viscosity | Density | Dielectric Constant |
| --- | --- | --- | --- |
| Water | Small Increase | Small Increase | Large Increase |
| Urea | Small Change | Small Change | Large Change |
| Glycerol | Large Increase | Small Increase | Large Change |
| Methanol | No Change | No Change | Medium Change |
| Sulfur | No Change | No Change | Small Increase |

It can be seen from the table that all kinds of contaminants have an effect on the dielectric constant of the fuel. The fuel quality can therefore be estimated electronically by measuring changes in the dielectric constant of the fuel under test. Although several different types of electronic fuel sensors measuring capacitance are known, if the amount of contamination is small, the change in the dielectric constant will also be very small. Also, the dielectric constant of the fuel is also affected by temperature change, so that one has to measure the temperature separately with a temperature sensor, which increases the complexity and cost, and still has an inherent lack of accuracy without dielectric constant characterization curves at all temperatures with different contamination levels. Thus, a fuel quality sensor solving the aforementioned problems is desired.

SUMMARY

The fuel quality sensor detects contamination in fuel flowing in a conduit using electromagnetic energy tunneling to detect small changes in both the dielectric constant (Dk or relative permittivity) and Tan δ (the loss tangent of the dielectric material) of the flowing fuel. The fuel quality sensor includes two rectangular parallelepiped waveguides of equal dimensions stacked one atop the other and having a common ground. A thin wire extends through the intermediate wall(s) between the upper and lower waveguide cavities. An input connector is mounted on a sidewall of the upper waveguide, and an output connector is mounted on a sidewall of the lower waveguide cavity. A fluid conduit extends through the upper waveguide cavity adjacent the wire. A tunable microwave signal or wideband time domain pulse is applied to the input connector while fuel is flowing through the conduit. If the fuel flowing in the conduit is uncontaminated, the output signal at the second connector will show no change from the tunneling frequency, but if the fuel is contaminated, the change in the fuel's dielectric constant will result in a change in the tunneling frequency and/or tan δ at the second connector.

By observing the frequency shift and amplitude of the received electromagnetic energy from the transmitted electromagnetic energy, the dielectric permittivity and Tan δ of the fuel can be determined. By comparing the dielectric permittivity and Tan δ of the flowing fuel to known values for pure fuel and various contaminants, the amount and type of contamination can be determined.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The fuel quality sensor detects contamination in fuel flowing in a conduit using electromagnetic energy tunneling to detect small changes in both the dielectric constant (Dk or relative permittivity) and Tan δ (the loss tangent of the dielectric material) of the flowing fuel. The fuel quality sensor includes two rectangular parallelepiped waveguides of equal dimensions stacked one atop the other and having a common ground. A thin wire extends through the intermediate wall(s) between the upper and lower waveguide cavities. An input connector is mounted on a sidewall of the upper waveguide, and an output connector is mounted on a sidewall of the lower waveguide cavity. A fluid conduit extends through the upper waveguide cavity adjacent the wire. A tunable microwave signal or wideband time domain pulse is applied to the input connector while fuel is flowing through the conduit. If the fuel flowing in the conduit is uncontaminated, the output signal at the second connector will show no change from the tunneling frequency, but if the fuel is contaminated, the change in the fuel's dielectric constant will result in a change in tunneling frequency and/or tan δ at the second connector.

By observing the frequency shift and amplitude of the received electromagnetic energy from the transmitted electromagnetic energy, the dielectric permittivity and Tan δ of the fuel can be determined. By comparing the dielectric permittivity and Tan δ of the flowing fuel to known values for pure fuel and various contaminants, the amount and type of contamination can be determined.

Figure 1:
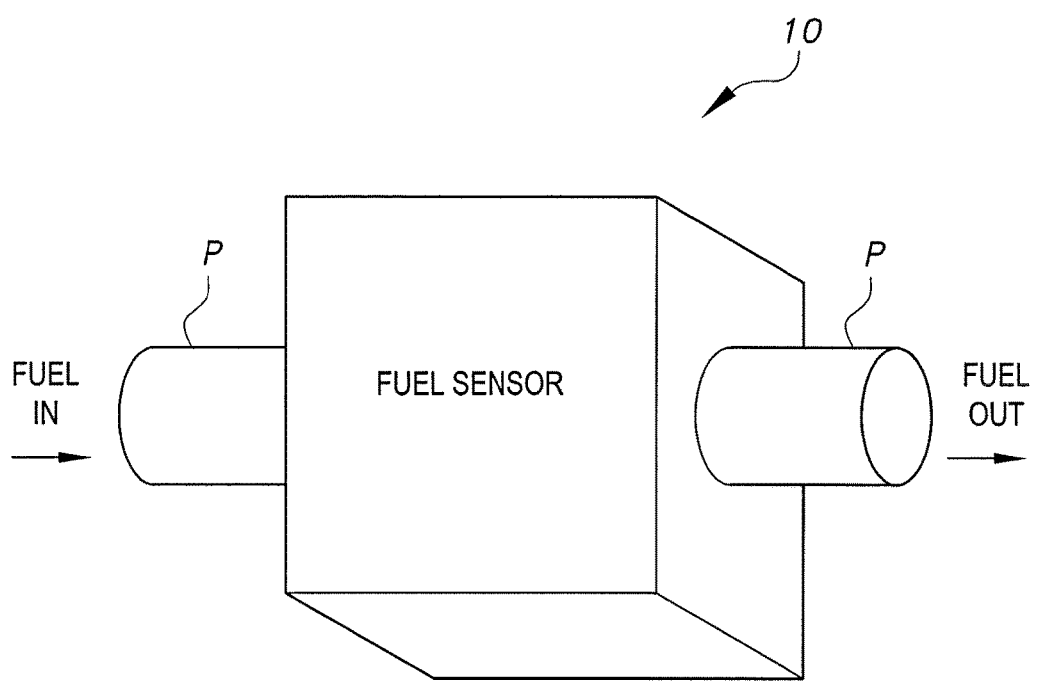
FIG. 1 is a diagrammatic environmental perspective view of a fuel quality sensor.
Figure 2:
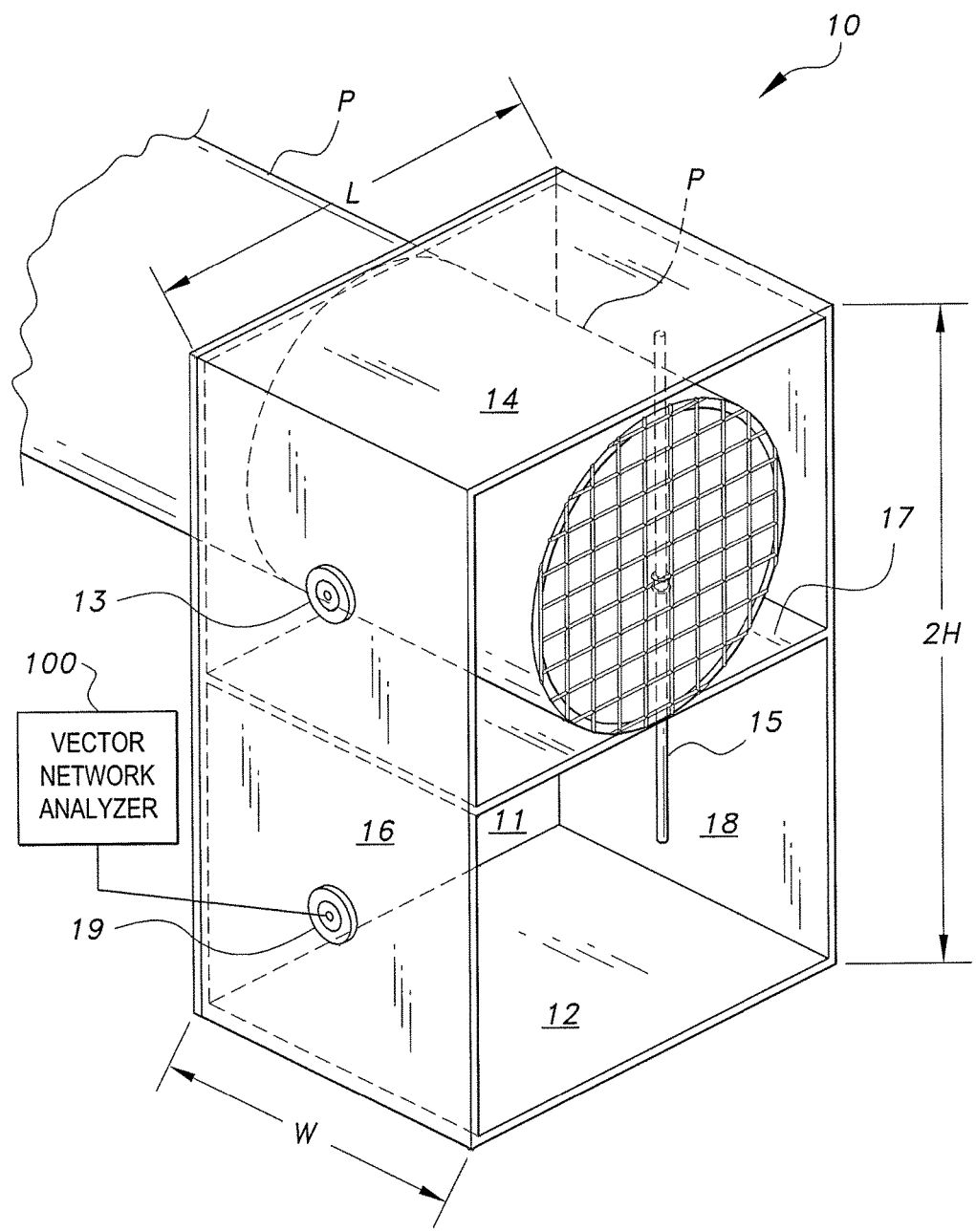
FIG. 2 is a diagrammatic perspective view of the fuel quality sensor as seen from the rear, the rear wall(s) of the waveguides being removed and the fuel conduit being truncated to show details thereof.
Figure 3:
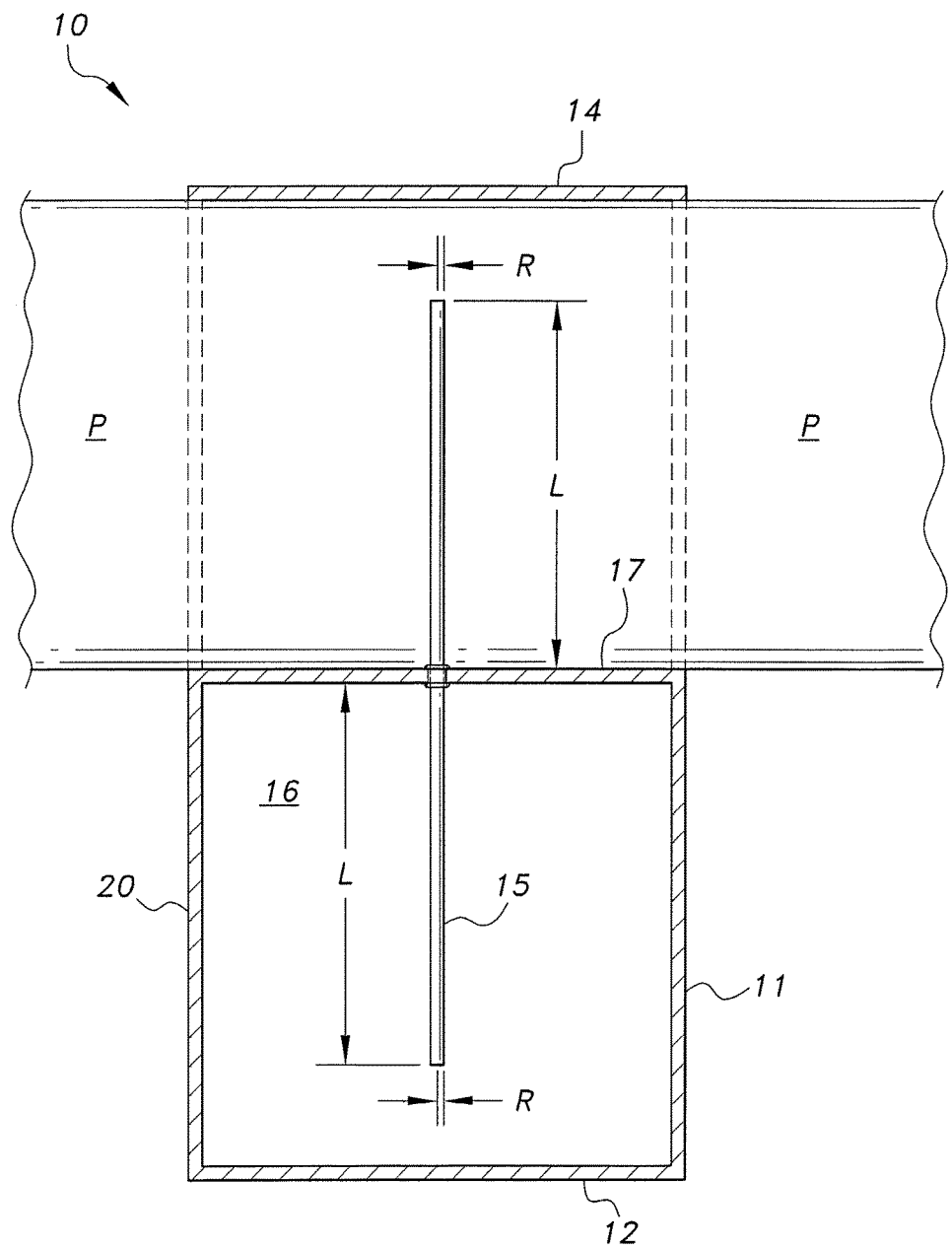
FIG. 3 is a side view in section of the fuel quality sensor of FIG. 1.
Figure 4:
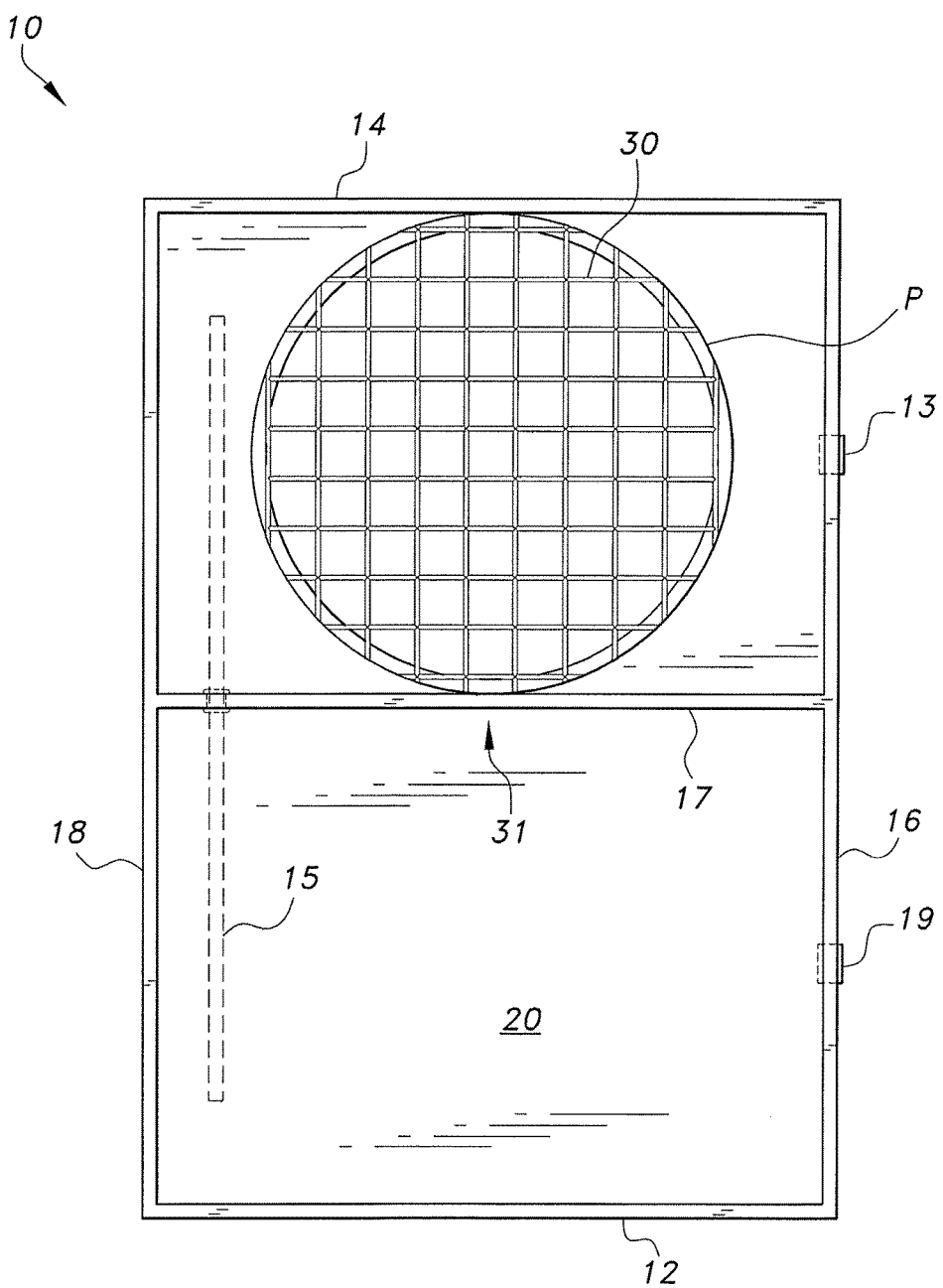
FIG. 4 is a front view of the fuel quality sensor of FIG. 1.

Referring to FIG. 1, the fuel quality sensor 10 measures the dielectric properties of fuel flowing through a conduit, such as a pipe P or fuel line, which may be made of rubber, plastic, or other electrically nonconductive material. As shown in FIGS. 2-4, the fuel quality sensor 10 includes an upper waveguide having a top plate 14, a first side plate 16, a second side plate 18, a front plate 11, a back plate 20, and a first bottom or intermediate plate 17. The sensor 10 further includes an adjacent lower waveguide that shares the first side plate 16, the second side plate 18, the front plate 11 and the back plate 20 with the first waveguide and further includes a second bottom plate 12. The intermediate plate 17 that defines the bottom plate of the upper waveguide also forms a top plate of the lower waveguide. The upper waveguide and the lower waveguide have the same dimensions so that they resonate at the same frequency. Although the sensor is shown in the drawings having a single waveguide housing bisected by the intermediate plate 17 to define two waveguides, it will be understood that the sensor 10 may be formed by two separate waveguides in which the top plate of the lower waveguide is bonded or clamped to the bottom plate of the upper waveguide. The walls or plates of the waveguide are formed of aluminum or other electrically conductive metal.

A metallic wire 15 or rod of relatively thin diameter extends through the intermediate plate(s) 17 from the interior cavity of the upper waveguide into the interior cavity of the lower waveguide. The metallic wire 15 is electrically isolated from the first bottom plate 17, as is described further below. An input port 13 including a radiator and a coaxial cable connector (shown diagrammatically in the drawings) is mounted in the first side plate 16 so that the radiator extend into the interior cavity of the upper waveguide for introducing a microwave signal into the first waveguide. An output port 19 including a receiver element and a coaxial cable connector (shown diagrammatically in the drawings) is mounted in the first side plate 16 so that the receiver (a disk or the like) extends into the interior of the lower waveguide for receiving the microwave signal that tunnels through the wire 15 from the upper waveguide into the lower waveguide after being modified by the capacitance of the fuel flowing through the pipe P. Each waveguide has a height H, length L and width W. the plates are all metallic and are preferably made of aluminum.

The rubber or plastic fuel conduit P extends through the front plate 11, the interior cavity of the upper waveguide, and the back plate 20. A metallic conductive gauze 30 extends across the interior of the fuel conduit P where it passes through the front plate 11 and the back plate 20 and is arranged perpendicular to the longitudinal axis of the fuel conduit P and the path of the fuel flowing in the conduit P. The metallic conductive gauze 30 is electrically connected to the housing of the waveguide by passing through the fuel conduit P to connect to the intermediate plate 17 at point 31. The metallic conductive gauze 30 is composed of a plurality of conductive wires arranged perpendicular to each other, similar to a metallic screen. The physical pitch (distance between adjacent wires) of the metallic conductive gauze 30 is less than one-tenth the wavelength ($\lambda_o/10$) of the electromagnetic energy supplied to the input port, as described below.

Figure 5:
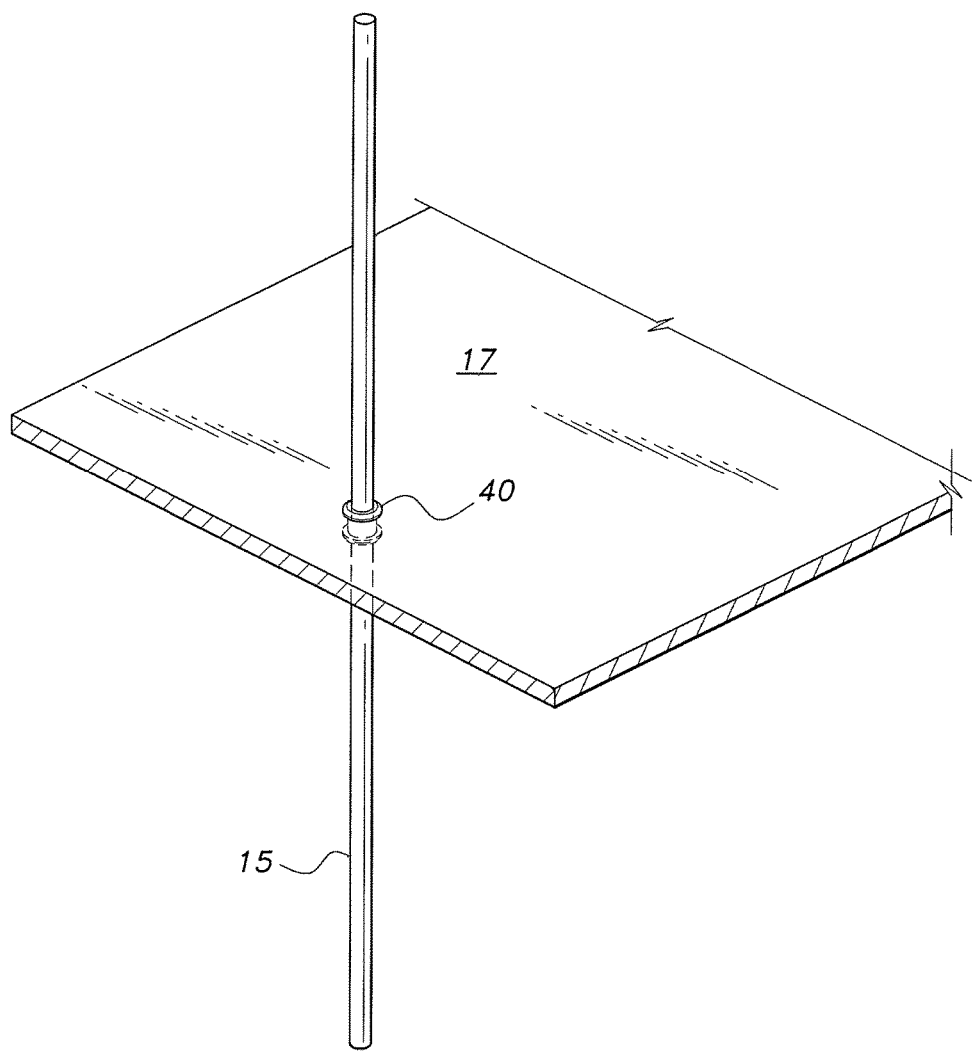
FIG. 5 is a partial view in section of the intermediate wall(s) of the fuel quality sensor of FIG. 1, showing the wire extending between the two waveguide cavities.

As best seen in FIG. 3, the metallic wire 15 extends a length L into the interior cavity of the upper waveguide and extends this same length L into the interior cavity of the lower waveguide. The metallic wire has a radius R. The length L and the radius R of the wire 15 can be adjusted to tune the sensor 10 depending on the wavelength 2 of the electromagnetic energy supplied to the input port 13. The electrical isolation of metallic wire 15 from the intermediate plate 17 is best seen in FIG. 5. The intermediate plate 17 includes an orifice with an insulating ring 40 or rubber grommet positioned within the orifice. The insulating ring 40 also includes an orifice through which the metallic wire 15 extends. In this manner, the insulating ring electrically isolates the metallic wire 15 from the intermediate plate 17, while also providing support for the wire 15.

A method of using the fuel quality sensor 10 includes transmitting electromagnetic energy having a first wavelength $\lambda_o$ into the interior cavity of the first waveguide through the input port 13, using an RF generator (not shown), as is known in the art. Electromagnetic energy at a second wavelength $\lambda_t$ then tunnels into and radiates inside the interior cavity of the second waveguide through the wire 15 and is received through the output port 19. The received electromagnetic energy is sent to a spectrum analyzer, vector network analyzer 100, or other electronic measurement device (not shown) for analyzing any frequency shift between the transmitted and received electromagnetic energy, as is further described below.

The energy tunneling (ET)-based fuel quality sensor 10 provides data to compute both the relative dielectric permittivity (Dk) and Tan δ (also called loss tangent) of the flowing fuel under test in conjunction with an analyzer. The fuel quality sensor 10 measures the shift in tunneling frequency and corresponding reduction in amplitude of the coupled energy due to the dielectric permittivity and Tan δ of fuel under test. Pure fuel and all types of contamination like water, have their own unique dielectric permittivity and Tan δ. For example, the dielectric constant of water is 80 and Tan δ is 0.157. Therefore, the type and amount of contamination can be determined by measuring Dk and Tan δ of the fuel sample under test and comparing it to known values. The known values can be obtained by using the sensor 10 to test known fuels (with and without contaminates) and recording the results, or from a reference lookup table stored in memory in the analyzer.

Figure 6:
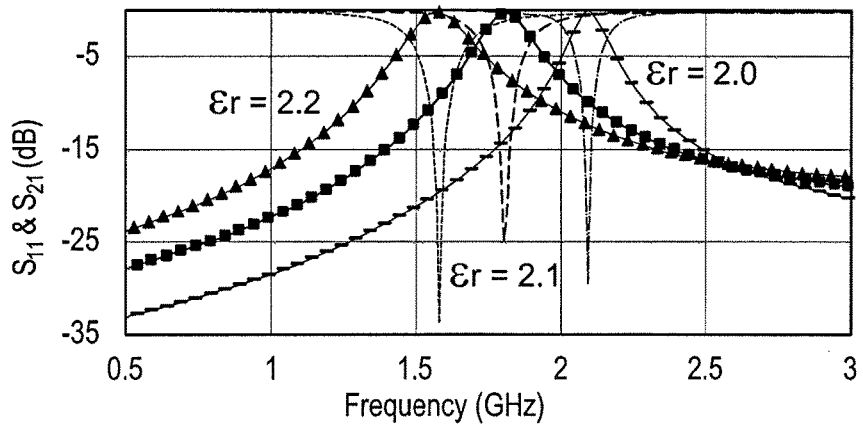
FIG. 6 is a plot of the s-parameters S11 and S21 as a function of frequency, showing that a change in fuel permittivity (dielectric constant, or Dk) from 2.0 to 2.1 results in a 500 MHz shift in tunneling frequency.
Figure 7:
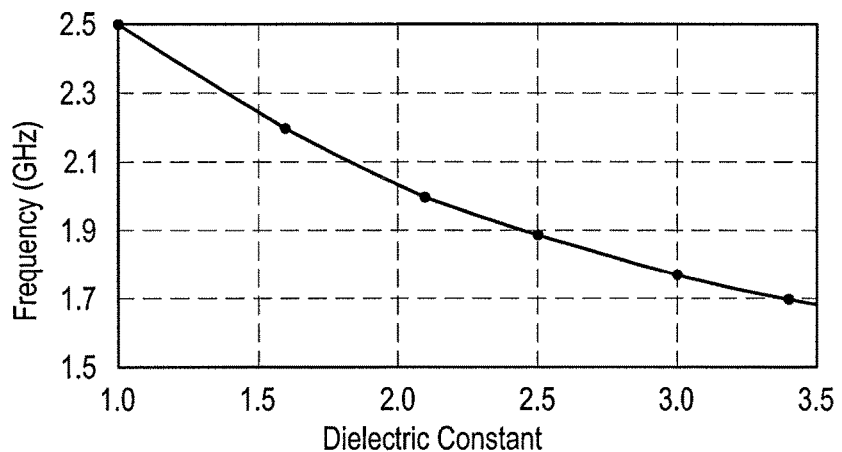
FIG. 7 is a plot of frequency versus dielectric constant, showing the change in tunneling frequency caused by a change in fuel dielectric constant.
Figure 8:
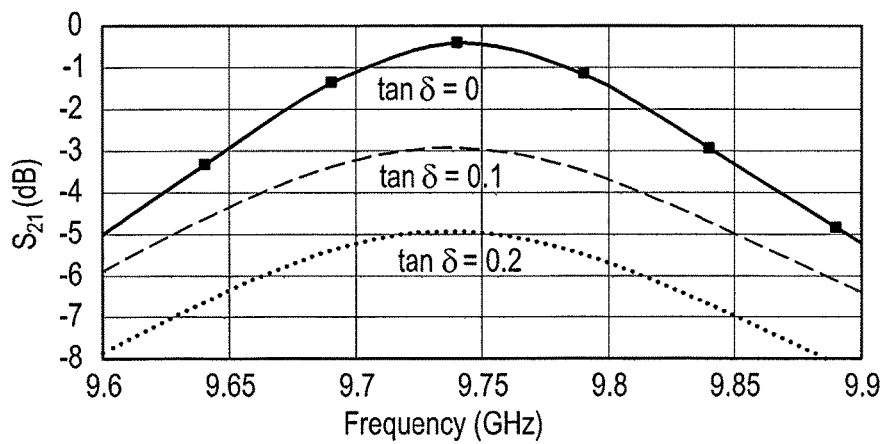
FIG. 8 is a plot of $S_{21}$ parameter (transmission coefficient) versus frequency, showing the effect of change in loss tangent (Tan δ) on amplitude.

As shown in the simulations plotted in FIGS. 6-8, a change in the relative permittivity (εr) of the material (fuel sample) from 2.0 to 2.1 results in a large shift of 500 MHz in the response curve of the (tunneling) frequency of the electromagnetic energy received at output port 19 from the frequency of the electromagnetic energy transmitted into input port 13. FIG. 7 shows a simplified relationship between the change in dielectric constant (which can be considered the same as the relative permittivity in this application) and the tunneling frequency. FIG. 8 shows how the amplitude of energy coupled between waveguides depends upon the Tan δ of the fuel sample under test. This large shift in tunneling frequency with a small change in relative permittivity of the fuel and reduction of amplitude with an increase in Tan δ provides for a highly sensitive fuel sensor.

Changes in temperature may change the viscosity, conductance, capacitance, and the relative permittivity of the material (fuel). This is tough challenge in all existing electronic fuel sensors. For example, at 25° C. the relative permittivity of diesel fuel is 2.1, while at 60° C. the permittivity decreases to 1.98. This temperature condition is normal in many tropical countries. The fuel quality sensor 10 provides a unique but simple technique to calibrate, and thus compensate, the relative permittivity changes with temperature. The technique includes using two of the fuel quality sensors 10 excited by the same electromagnetic energy source. A first sensor 10 is filled with a known pure fuel sample (gold sample). The first sensor 10 may include a closed pipe P such that the fuel gold sample need not be a large sample, since it is not flowing. The second sensor 10 has a continuous flow of the fuel under test. The frequency used is in GHz range, and the flow velocity of fuel is small, such that all the fuel samples appear static to the GHz electromagnetic energy. As the temperature conditions are the same for both of the sensors 10, the tunneling frequency and Tan δ of the first sensor with the gold sample is used as a reference for the tunneling frequency. If the tunneling frequencies and Tan δ of both sensors are the same, it indicates that the sample under test is uncontaminated and good for use. If the tunneling frequency and/or Tan δ of both sensors 10 are not same, it indicates that the sample under test is contaminated. The amount of impurities in the sample under test can be estimated by the value of the change in frequency (Δf) and the change in Tan δ (Δ Tan δ). Large Δf and Δ Tan δ indicates a large amount of contamination in the fuel sample.

Figure 9:
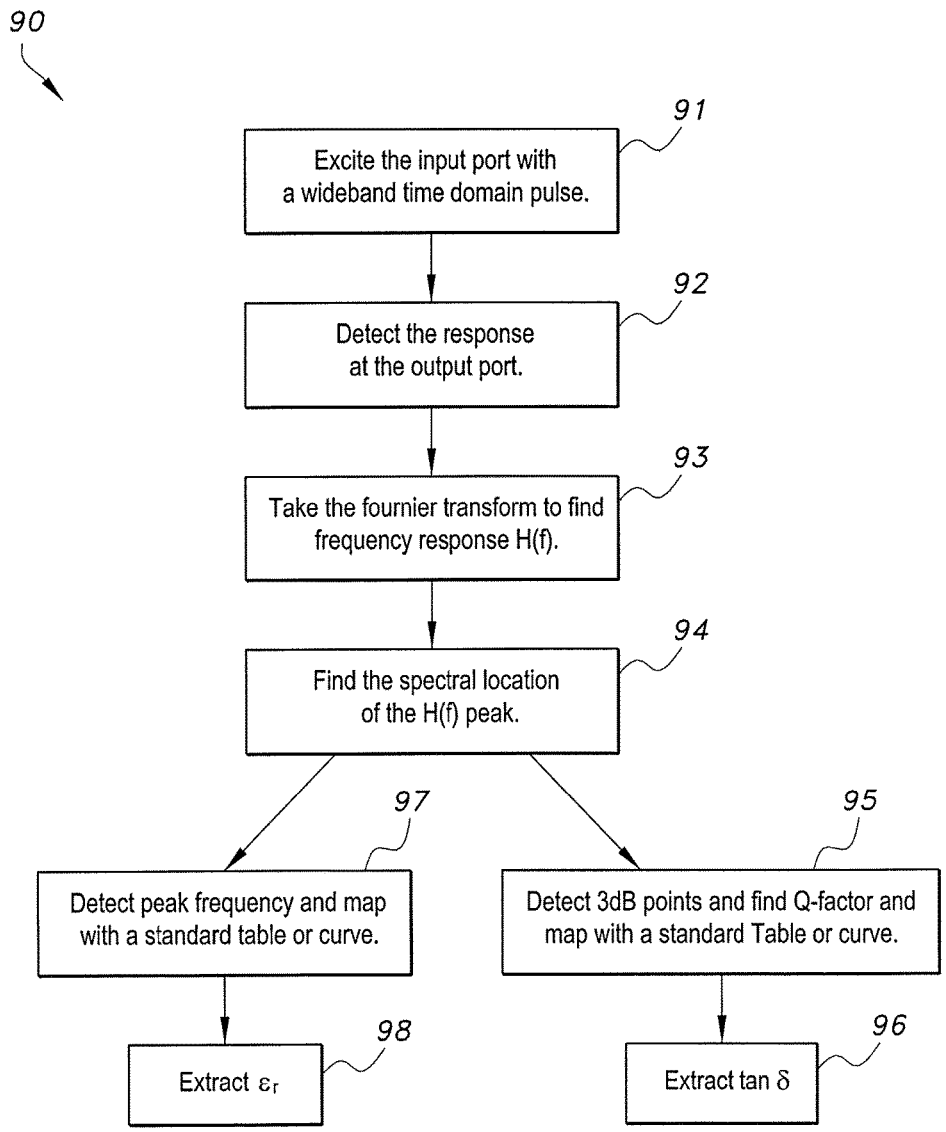
FIG. 9 is a flowchart illustrating a method of using the fuel sensor of FIG. 1.

FIG. 9 is a flow chart 90 illustrating a method of using the fuel sensor 10. In a first step 91 the input port 13 is excited with a wideband time domain pulse. In a second step 92, the response is detected at the output port 19 using the vector network analyzer 100. In a third step 93, the Fourier transform of the received signal is taken to find the frequency response H(f) of the received signal. In a fourth step 94, the spectral location of the H(f) peak is located. In a fifth step 95, the 3 dB points are detected and the Q-factor is determined using a standard table or curve. In a sixth step 96, the 3 dB and Q-factor are used to extract Tan δ. In a seventh step 97, the peak frequency is detected and mapped using a standard table or curve. In an eighth step 98, the peak frequency is used to extract relative permittivity (εr).

It is to be understood that the fuel quality sensor is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A fuel quality sensor for electronically monitoring contamination in flowing fuel in real time, comprising:
    an upper waveguide and a lower waveguide, the waveguides being rectangular parallelepipeds defining interior cavities resonant at the same frequency and having at least one intermediate plate separating the upper waveguide from the lower waveguide, the waveguides being short circuited and having a common ground;
    a thin metallic wire extending through the intermediate plate from the interior cavity of the upper waveguide into the interior cavity of the lower waveguide, the metallic wire being electrically isolated from the at least one intermediate plate, the wire extending equal distances into the cavities;
    an input port mounted on the upper waveguide and having a radiator disposed in the interior cavity of the upper waveguide;
    an output port mounted on the lower waveguide and having a receiver disposed in the interior cavity of the lower waveguide; and
    a fuel conduit extending through the upper waveguide, the metallic wire being external to and in close proximity to the fluid conduit;
    wherein the metallic wire is dimensioned and configured for tunneling electromagnetic energy from the upper waveguide into the lower waveguide so that an output signal produced at the output port may be analyzed to determine a dielectric constant and loss tangent of fuel flowing in the fuel conduit for fuel contamination.

2. The fuel quality sensor according to claim 1, wherein said upper waveguide and said lower waveguide are each made of aluminum.

3. The fuel quality sensor according to claim 1, wherein said fuel conduit is made of electrically non-conductive material.

4. The fuel quality sensor according to claim 1, further comprising a grommet mounted in the at least one intermediate plate, said thin metallic wire extending through the grommet, the grommet insulating the thin metallic wire from said at least one intermediate plate.

5. The fuel quality sensor according to claim 1, wherein said upper waveguide and said lower waveguide comprise a single rectangular parallelepiped housing and said at least one intermediate plate consists of a single intermediate plate bisecting the single rectangular parallelepiped housing to define said upper waveguide and said lower waveguide.

6. The fuel quality sensor according to claim 1, wherein said upper waveguide comprises a first rectangular parallelepiped housing having a bottom plate and said lower waveguide comprises a second rectangular parallelepiped housing having a top plate, the bottom plate of said upper waveguide overlying the top plate of said lower waveguide, whereby said at least one intermediate plate comprises the overlying bottom and top plates.

7. The fuel quality sensor according to claim 1, wherein said upper waveguide comprises a front plate and a back plate, said fuel conduit extending through the front plate and the back plate of said upper waveguide, the fuel quality sensor further comprising:
    a first metallic, electrically conductive gauze patch extending transversely across said fluid conduit coplanar with and electrically connected to the front plate; and
    a second metallic, electrically conductive gauze patch extending transversely across said fluid conduit coplanar with and electrically connected to the back plate.

8. The fuel quality sensor as recited in claim 7, wherein said first and second gauze patches have a pitch less than $\lambda_0/10$, where $\lambda_0$ is the wavelength of a microwave signal applied to said input port.

9. The fuel quality sensor as recited in claim 1, wherein said thin metallic wire has a radius and a length defining the resonant frequency of the electromagnetic energy tunneling from said upper waveguide cavity into said lower waveguide cavity.

10. The fuel quality sensor as recited in claim 1, further comprising a vector network analyzer connected to said output port.

11. The fuel quality sensor as recited in claim 1, further comprising an RF detection and processing circuit connected to said output port.

* * * * *